(12) United States Patent
Barel et al.

(10) Patent No.: US 11,856,936 B2
(45) Date of Patent: Jan. 2, 2024

(54) DISINFECTION OF SOIL BY APPLICATION OF ELECTRIC VOLTAGE

(71) Applicant: CLEAN SOIL AGRO LTD., Or-Haner (IL)

(72) Inventors: Nimrod Barel, Mishmar Ayalon (IL); Yoram Lebovits, Givat Brenner (IL); Uri Yaffe, Or-Haner (IL); Oded Yaffe, Rehovot (IL); Eli Yaish, Moshav Ein Habsor (IL)

(73) Assignee: CLEAN SOIL AGRO LTD., Or-Haner (IL)

( * ) Notice: Subject to any disclaimer, the term of this patent is extended or adjusted under 35 U.S.C. 154(b) by 0 days.

(21) Appl. No.: 17/796,168

(22) PCT Filed: Jan. 29, 2021

(86) PCT No.: PCT/IL2021/050105
§ 371 (c)(1),
(2) Date: Jul. 28, 2022

(87) PCT Pub. No.: WO2021/152594
PCT Pub. Date: Aug. 5, 2021

(65) Prior Publication Data
US 2023/0098648 A1 Mar. 30, 2023

(30) Foreign Application Priority Data
Jan. 30, 2020 (IL) .......................................... 272383

(51) Int. Cl.
*A01B 47/00* (2006.01)
*B09C 1/00* (2006.01)
(Continued)

(52) U.S. Cl.
CPC .............. *A01M 19/00* (2013.01); *A01B 47/00* (2013.01); *A01M 17/00* (2013.01); *A61L 2/03* (2013.01);
(Continued)

(58) Field of Classification Search
CPC ........... A01B 47/00; B09C 1/06; B09C 1/062; B09C 1/085; B09C 2101/00; A01M 19/00;
(Continued)

(56) References Cited

U.S. PATENT DOCUMENTS 2,429,412 A 10/1947 Keller
2,484,443 A * 10/1949 Baker ................. A01M 21/046
47/1.3
(Continued)

FOREIGN PATENT DOCUMENTS

CN 1829436 A 9/2006
CN 105454215 A 4/2016
(Continued)

OTHER PUBLICATIONS

Ometsinskij et al; SU 14420958 A1 machine translation; all; Dec. 1988 (Year: 1988).*
(Continued)

*Primary Examiner* — Benjamin F Fiorello
(74) *Attorney, Agent, or Firm* — The Roy Gross Law Firm, LLC; Roy Gross

(57) ABSTRACT

A soil disinfector comprising an insulating endless belt with at least one row of positive electrodes and at least one row of negative electrodes mounted on the endless belt. The electrodes are mounted with their heads on the inside of the belt and their bodies pointing outward from the belt, the electrodes being configured to penetrate the soil. The electrodes take their power from a power source, the power
(Continued)

source being connected to the electrodes via sets of rows of rollers and sets of rows of stationary conductive contact plates, at least one set of each being positive and at least one set of each being negative. The soil disinfector also has sensors to detect soil conditions and a processor to alter power applied to the soil based on the soil conditions.

20 Claims, 13 Drawing Sheets

(51) Int. Cl.
    *A01M 19/00*     (2006.01)
    *A01M 17/00*     (2006.01)
    *A61L 2/03*     (2006.01)
    *A61L 2/24*     (2006.01)

(52) U.S. Cl.
    CPC ............... *A61L 2/24* (2013.01); *B09C 1/00* (2013.01); *A61L 2202/14* (2013.01); *B09C 2101/00* (2013.01)

(58) Field of Classification Search
    CPC .. A01M 17/00; A61L 2/00; A61L 2/24; A61L 2202/14
    See application file for complete search history.

(56) References Cited

U.S. PATENT DOCUMENTS

| | | | | |
|---|---|---|---|---|
| 3,919,806 | A * | 11/1975 | Pluenneke | A01M 21/046 47/1.3 |
| 4,177,603 | A * | 12/1979 | Dykes | A01M 21/046 47/1.3 |
| 4,428,150 | A * | 1/1984 | Geiersbach | A01M 21/046 47/1.3 |
| 9,936,686 | B2 * | 4/2018 | Crisp | A01M 21/046 |
| 10,188,045 | B1 | 1/2019 | Flagler et al. | |
| 11,266,140 | B2 * | 3/2022 | Kroeger | A01M 21/046 |
| 2003/0150156 | A1 * | 8/2003 | Flagler | A01M 19/00 47/1.3 |
| 2016/0050902 | A1 | 2/2016 | Crisp et al. | |
| 2017/0113743 | A1 | 4/2017 | Kirchmair et al. | |
| 2017/0202202 | A1 | 7/2017 | Crisp et al. | |

FOREIGN PATENT DOCUMENTS

| | | | |
|---|---|---|---|
| CN | 105613469 A | 6/2016 | |
| CN | 105613470 A | 6/2016 | |
| CN | 205813390 U | 12/2016 | |
| SU | 1442095 A1 * | 12/1988 | ............. A01B 47/00 |
| WO | 2009/048190 A2 | 4/2009 | |
| WO | 2014/114899 A1 | 7/2014 | |

OTHER PUBLICATIONS

PCT International Search Report for International Application No. PCT/IL2021/050105, dated Jul. 4, 2021, 7pp.
PCT Written Opinion for International Application No. PCT/IL2021/050105, dated Jul. 4, 2021, 11pp.
PCT Preliminary Report on Patentability for International Application No. PCT/IL2021/050105, dated Feb. 23, 2022, 6 pp.
Chinese Office Action for Application No. 202180026617.9, dated May 7, 2023, 9pp.

* cited by examiner

DISINFECTION OF SOIL BY APPLICATION OF ELECTRIC VOLTAGE

CROSS REFERENCE TO RELATED APPLICATIONS

This application is a National Phase of PCT Patent Application No. PCT/IL2021/050105 having International filing date of Jan. 29, 2021, which claims the benefit of priority of Israeli Patent Application No. 272383, filed Jan. 30, 2020 the contents of which are all incorporated herein by reference in their entirety.

FIELD OF THE INVENTION

The present invention generally pertains to a system and method for destroying microorganisms in soil using electric voltage.

BACKGROUND OF THE INVENTION

In agricultural soils used for intensive crops, pathogens and non-crop growth such as weeds often develop that impair crop yield, reduce crop growth rate and reduce crop quality and quantity. The pathogens include nematodes, insects, mites, bacteria, fungi and viruses, most of which are land dwellers and most of which have found ways to persist in the soil from season to season.

Until 2005, methyl bromide was widely used for soil disinfection. It provided a good and inexpensive solution to prevent growth of most of the land-dwelling pathogens and therefore enabled large-scale farmers to have good crop yields.

One technique that can be applied without fear of leaving environmentally damaging residues in the soil is disinfecting the soil via applying an electric current through the soil to be disinfected, with voltage and current sufficient to kill the pathogens therein.

Since 2005, the use of methyl bromide has been gradually reduced due to its toxicity and the environmental damage it can cause, resulting in a search for efficient, friendly and economical solutions to the problem of reducing or eliminating the pathogens.

U.S. Pat. No. 2,429,412 discloses a system, an apparatus and method of operation, enabled to apply intense electrical treatment to the soil to a considerable depth, the depth of treatment being only limited by the depth to which it is practicable to run a series or set of soil distributing electrodes. The depth of treatment is thus limited in practice only by such physical considerations as those which are ordinarily taken into account in determining maximum practicable depth of soil disturbance.

However, U.S. Pat. No. 2,429,412 requires two sets of horizontal plates, the plates arranged in rows, with staggered rows for at least one set of plates and one set of plates passing through the ground at a depth beneath the surface, with all disinfection between the surface and the lower set of plates.

CN205813390 discloses a soil electric disinfection and pest control device, comprising two electrode plates arranged on the ground of a vegetable greenhouse. The soil electric disinfection and pest control device of the present invention comprises two electrode plate slots disposed on the ground of a vegetable greenhouse and a fixing rod fixed on the top of the vegetable greenhouse, and two electrodes. The plate slots are disposed in a parallel structure. The fixing rods are disposed laterally. The lower end of the fixing rods is provided with a rotating rod. The rotating rods and the fixed rods are arranged in a parallel structure. The bearing ring is fixedly connected to the outer ring surface of the rotating rod. The inner ring of the bearing is fixedly mounted with a supporting rod, and the supporting rod is fixedly mounted on the outer ring of the bearing. The upper end is connected to the fixed rod and the two rotating discs are fixedly mounted on the rotating rod. The lower end of the reel is provided with an electrode plate protection shell, the electrode plate protection shell and the reel are oppositely disposed, and the lower end of the electrode plate protection shell is open. A cover plate is fixedly mounted on the lower end of the electrode plate protective case through a hydraulic hinge. The upper end of the electrode plate protective case is provided with a through hole, and the electrode plate protective case is provided with an electrode plate.

However, CN205813390 requires two sets of horizontal plates with the plates arranged in rows, a lower set of plates at ground level and an upper set of plates at a height near the top of a greenhouse. The device is stationary; there is neither teaching nor suggestion that the device can be transported horizontally during use. Furthermore, disinfection occurs for soil above the ground; if one set of plates were buried, disinfection would occur below ground but it would not be practicable for the device to be movable in use.

It is therefore a long felt need to provide a soil disinfection system which does not require to be used in a fixed position and does not require a set of horizontal plate electrodes at a depth under the ground.

SUMMARY OF THE INVENTION

It is an object of the present invention to disclose a system for destroying microorganisms in soil using electric voltage.

It is another object of the present invention to disclose a motorized tracked vehicle for driving on land comprising
  an endless belt in mechanical contact with at least one propulsion roller, said endless belt being insulating;
  at least one sensor for detecting soil data, said sensor mounted on said vehicle;
  at least one row of positive electrodes mounted on said endless belt for administering positive current and positive voltage to soil, each of said at least one row of positive electrodes comprising at least one positive electrode;
  at least one row of negative electrodes mounted on said endless belt for administering negative current and negative voltage to soil, each of said at least one row of negative electrodes comprising at least one negative electrode;
  an electrical power source for providing said positive current and said positive voltage to a portion of said at least one row of positive electrodes and said negative current and said negative voltage to a portion of said at least one row of negative electrodes;
  at least one row of positive power rollers, said at least one row of positive power rollers being in electrical communication with at least one positive terminal of said electrical power source;
  at least one row of negative power rollers, said at least one row of negative power rollers being in electrical communication with at least one negative terminal of said electrical power source;
  at least one row of positive contact plates in electrical communication with each of said at least one row of positive power rollers; each of said at least one row of positive contact plates configured to be in electrical communication with at least a portion of at least one of said at least one row of positive electrodes; and at least one row of negative contact plates in electrical communication with each of said at least one row of negative power rollers; each of said at least one row of negative contact plates configured to be in electrical communication with at least a portion of at least one of said at least one row of negative electrodes;

a processor for processing soil data collected by said sensor;

wherein said at least one row of positive power rollers and said at least one row of positive contact plates are configured to administer said positive current and said positive voltage to a portion of said at least one row of positive electrodes, said portion of said at least one row of positive electrodes being configured to be embedded in said soil during said administration of said positive current and said positive voltage; and said at least one row of negative power rollers and said at least one row of negative contact plates are configured to administer said negative current and said negative voltage to a portion of said at least one row of negative electrodes, said portion of said at least one row of negative electrodes being configured to be embedded in said soil during said administration of said negative current and said negative voltage; and said at least one processor is configured to determine from said soil data transmitted by said sensors, a value for each set of applied power selected from a group consisting of voltage, current, power level and any combination thereof required to kill or disable at least one type of pathogen; and to instruct said electrical power source to apply said set of applied power to said at least one positive electrode and said at least one negative electrode.

It is another object of the present invention to disclose the motorized tracked vehicle as described above, wherein a width of said endless belt is 160 cm.

It is another object of the present invention to disclose the motorized tracked vehicle as described above, wherein a width of said endless belt is in a range from 50 cm to 800 cm.

It is another object of the present invention to disclose the motorized tracked vehicle as described above, wherein the endless belt has a length in a range between 3 m and 15 m.

It is another object of the present invention to disclose the motorized tracked vehicle as described above, wherein the endless belt has a length of 6 m.

It is another object of the present invention to disclose the motorized tracked vehicle as described above, wherein the at least one sensor is selected from a group consisting of humidity sensor, the conductivity sensor, temperature sensor, voltage sensor, current sensor, power level sensor, and any combination thereof.

It is another object of the present invention to disclose the motorized tracked vehicle as described above, wherein an absolute value of a voltage applicable all of said at least one positive electrode and all of said at least one negative electrode and any combination thereof is in a range from 1000 V to 9000 V.

It is another object of the present invention to disclose the motorized tracked vehicle as described above, wherein an absolute value of a voltage applicable to all of said at least one positive electrode and all of said at least one negative electrode is 3000 V.

It is another object of the present invention to disclose the motorized tracked vehicle as described above, wherein a power level applicable to all of said at least one positive electrode and all of said at least one negative electrode is in a range from 20000 W to 60,000 W.

It is another object of the present invention to disclose the motorized tracked vehicle as described above, wherein a power level applicable to all of said at least one positive electrode and all of said at least one negative electrode is in a range from 30,000 W to 50,000 W.

It is another object of the present invention to disclose the motorized tracked vehicle as described above, wherein a power level applicable to all of said at least one positive electrode and all of said at least one negative electrode is 50,000 W.

It is another object of the present invention to disclose the motorized tracked vehicle as described above, wherein an absolute value of a current applicable to all of said at least one positive electrode and all of said at least one negative electrode is in a range from 1 A to 10 A.

It is another object of the present invention to disclose the motorized tracked vehicle as described above, wherein an absolute value of a current applicable to all of said at least one positive electrode and all of said at least one negative electrode is in a range from 5 A to 8 A.

It is another object of the present invention to disclose the motorized tracked vehicle as described above, additionally comprising at least one circuit breaker.

It is another object of the present invention to disclose the motorized tracked vehicle as described above, additionally comprising a controller.

It is another object of the present invention to disclose the motorized tracked vehicle as described above, wherein the controller is configured to display a member of a group consisting of display electrode voltage, load current, soil temperature, soil humidity, soil conductivity, track shoe temperature, electrode temperature, generator overload status, transformer overload status and any combination thereof.

It is another object of the present invention to disclose the motorized tracked vehicle as described above, wherein the controller is configured to provide at least one alert.

It is another object of the present invention to disclose the motorized tracked vehicle as described above, wherein the at least one alert is selected from a group consisting of alert as to the existence of a breakdown, alert as to the nature of the breakdown, alert as to the location in the system of the breakdown, alert of the probability of a breakdown, alert of an overload, alert of an electrical failure, alert of a short, alert of a failure of a power supply, alert of a failure in a transformer and any combination thereof.

It is another object of the present invention to disclose the motorized tracked vehicle as described above, wherein at least one of the following is true:

a. at least one member of a group consisting of said at least one positive electrode and said at least one negative electrode is configured to be heated to a temperature of at least 200 C;

b. said soil data is selected from a group consisting of humidity, temperature, conductivity and any combination thereof;

c. at least two of said linked track shoes have a flexible linkage;

d. said motorized tracked vehicle is configured to be operable in a manner selected from a group consisting of manually, autonomously and any combination thereof; and e. said motorized tracked vehicle is configured to be remotely controllable.

It is another object of the present invention to disclose the motorized tracked vehicle as described above, wherein a member of a group consisting of said at least one positive electrode, said at least one negative electrode and any combination thereof is configured to be heated by a method selected from a group consisting of induction heating, resistance heating, electric arc heating, dielectric heating and any combination thereof.

It is another object of the present invention to disclose the motorized tracked vehicle as described above, wherein a member of a group consisting of said at least one positive electrode, said at least one negative electrode and any combination thereof is configured to be heated by induction heating.

It is another object of the present invention to disclose the motorized tracked vehicle as described above, wherein a member of a group consisting of said at least one positive electrode, said at least one negative electrode and any combination thereof comprises a pin-like electrode or a spike-like electrode, said pin-line electrode or said spike-like electrode protruding substantially perpendicularly and outwardly from said track shoe.

It is another object of the present invention to disclose the motorized tracked vehicle as described above, wherein a length of a member of a group consisting of said at least one positive electrode, said at least one negative electrode and any combination thereof is 30 cm.

It is another object of the present invention to disclose the motorized tracked vehicle as described above, wherein a length of a member of a group consisting of said at least one positive electrode, said at least one negative electrode and any combination thereof is in a range from 15 cm to 50 cm.

It is another object of the present invention to disclose the motorized tracked vehicle as described above, wherein a diameter of a member of a group consisting of said at least one positive electrode, said at least one negative electrode and any combination thereof is 5 cm.

It is another object of the present invention to disclose the motorized tracked vehicle as described above, wherein a diameter of a member of a group consisting of said at least one positive electrode, said at least one negative electrode and any combination thereof is in a range from 1 cm to 10 cm.

It is another object of the present invention to disclose the motorized tracked vehicle as described above, wherein a center-to-center distance between an electrode in one row and an electrode in an adjacent row is in a range from 3 cm to 30 cm.

It is another object of the present invention to disclose the motorized tracked vehicle as described above, wherein a center-to-center distance between an electrode and a next trailing electrode is in a range from 3 cm to 30 cm.

It is another object of the present invention to disclose the motorized tracked vehicle as described above, wherein said power supply comprises at least one generator and at least one power unit.

It is another object of the present invention to disclose the motorized tracked vehicle as described above, wherein said at least one generator generates power at 220 VAC.

It is another object of the present invention to disclose the motorized tracked vehicle as described above, wherein said at least one power unit generates power at a power level of 5000 W.

It is another object of the present invention to disclose the motorized tracked vehicle as described above, wherein said power unit output power is in a range between 2000 W and 10000 W.

It is another object of the present invention to disclose the motorized tracked vehicle as described above, wherein said power unit output power is in a range between 3000 W and 6000 W.

It is another object of the present invention to disclose the motorized tracked vehicle as described above, wherein said power unit output power is 5000 W.

It is another object of the present invention to disclose the motorized tracked vehicle as described above, wherein said motorized tracked vehicle comprises a plurality of rollers.

It is another object of the present invention to disclose the motorized tracked vehicle as described above, wherein a plurality of propulsion rollers and said endless belt are configured to form a caterpillar-type tread.

It is another object of the present invention to disclose the motorized tracked vehicle as described above, wherein at least one motor is configured to rotate said at least one roller.

It is another object of the present invention to disclose the motorized tracked vehicle as described above, wherein said motorized tracked vehicle is either self-contained or is configured to be attachable to another vehicle.

It is another object of the present invention to disclose the motorized tracked vehicle as described above, wherein said attachment comprises electrical connectivity via a power take off (PTO).

It is another object of the present invention to disclose the motorized tracked vehicle as described above, wherein said land is selected from land in a group consisting of an open area or an enclosed space.

It is another object of the present invention to disclose the motorized tracked vehicle as described above, wherein said land in an open area is selected from a group consisting of a field, arable land, agricultural land, cropland, pasture, rangeland, grassland, shrubland, a nursery, an orchard, a garden, a lawn, forestry, silviculture, a sport field, cultivable land, a plantation, a berm, a verge, land requiring remediation, and any combination thereof.

It is another object of the present invention to disclose the motorized tracked vehicle as described above, wherein said land requiring remediation is selected from a group consisting of land requiring removal of plant-damaging pathogens, land requiring removal of animal-damaging pathogens, land requiring removal of chemicals and any combination thereof.

It is another object of the present invention to disclose the motorized tracked vehicle as described above, wherein said land in an enclosed space is selected from a group consisting a barn, a greenhouse, a stable, a dovecot, soil for indoor remediation and any combination thereof.

It is another object of the present invention to disclose the motorized tracked vehicle as described above, wherein said soil for indoor remediation is selected from a group consisting of soil from a vertical farming operation, soil from a greenhouse and any combination thereof.

It is another object of the present invention to disclose a trailed implement for electrically disinfecting a soil. The aforesaid trailed implement comprises: (a) a power supply configured for generating high voltage; (b) an electrode arrangement further comprising a base frame and at least two electrodes mounted therewithin and insertable into said soil; said electrodes are electrically connected to said high voltage power supply such that said high voltage is applied between said at least two electrodes. At least one of said electrodes is reciprocally movable relative to said base frame in a direction of trailing said implement.

It is another object of the present invention to disclose the trailed implement as described above, wherein at least two frame electrodes which are frame-shaped and comprise a top bar and a bottom bar oriented along said direction of trailing and a plurality of plate-like plow members mounted between said top and bottom bars and perpendicular thereto.

It is another object of the present invention to disclose the trailed implement as described above, wherein the plate-like plow members mounted at an angle relative to said direction of trailing ranging between 5 and 90°.

It is another object of the present invention to disclose the trailed implement as described above, wherein a power supply is configured for generating at least one of AC and DC high voltage.

It is another object of the present invention to disclose the trailed implement as described above, wherein a length L of said frame electrode along said direction of trailing ranging between 30 cm and 90 cm.

It is another object of the present invention to disclose the trailed implement as described above, wherein a height H of said frame-shaped electrode ranging between 15 cm and 60 cm.

It is another object of the present invention to disclose the trailed implement as described above, wherein a distance D between plate-like plow members within said frame-shaped electrode ranging between 4 cm and 10 cm.

It is another object of the present invention to disclose a motorized tracked vehicle for driving on land comprising
- at least one endless track in mechanical contact with at least one roller, said at least one endless track comprising a plurality of linked track shoes;
- at least one sensor for detecting soil data, said sensor mounted on said vehicle;
- at least two electrodes mounted on each of said at least one endless track for administering current and voltage to soil;
- a processor for processing soil data collected by said sensor; and
- an electrical power source for providing said current and said voltage to said at least two electrodes;
- wherein each of said at least two electrodes is pin-like or spike-like and each track shoe comprises at least one said soil penetrating pin-like or spike-like electrode protruding substantially perpendicularly and outwardly from said track shoe, said at least one processor configured to determine from said soil data transmitted by said sensors, a value for each set of applied power selected from a group consisting of voltage, current, power level and any combination thereof required to kill or disable at least one type of pathogen; and to instruct said electrical power source to apply said set of applied power to said at least two electrodes.

It is another object of the present invention to disclose the motorized tracked vehicle as described above, wherein all of the at least one endless track has a width in a range between 50 cm and 3 m.

It is another object of the present invention to disclose the motorized tracked vehicle as described above, wherein all of the at least one endless track has a width of 1.2 m.

It is another object of the present invention to disclose the motorized tracked vehicle as described above, wherein the at least one endless track has a length in a range between 3 m and 15 m.

It is another object of the present invention to disclose the motorized tracked vehicle as described above, wherein the at least one endless track has a length of 6 m.

It is another object of the present invention to disclose the motorized tracked vehicle as described above, wherein the at least one sensor is selected from a group consisting of humidity sensor, the conductivity sensor, temperature sensor, voltage sensor, current sensor, power level sensor, and any combination thereof.

It is another object of the present invention to disclose the motorized tracked vehicle as described above, wherein a voltage applicable to all of said at least two electrodes is in a range from 1000 V to 9000 V.

It is another object of the present invention to disclose the motorized tracked vehicle as described above, wherein a voltage applicable to all of said at least all of two electrodes is 3000 V.

It is another object of the present invention to disclose the motorized tracked vehicle as described above, wherein a power level applicable to all of said at least two electrodes is in a range from 20000 W to 60,000 W.

It is another object of the present invention to disclose the motorized tracked vehicle as described above, wherein a power level applicable to all of said at least two electrodes is in a range from 30,000 W to 50,000 W.

It is another object of the present invention to disclose the motorized tracked vehicle as described above, wherein a power level applicable to all of said at least two electrodes is 50,000 W.

It is another object of the present invention to disclose the motorized tracked vehicle as described above, wherein a current applicable to all of said at least two electrodes is in a range from 1 A to 10 A.

It is another object of the present invention to disclose the motorized tracked vehicle as described above, wherein a current applicable to all of said at least two electrodes is in a range from 5 A to 8 A.

It is another object of the present invention to disclose the motorized tracked vehicle as described above, additionally comprising at least one circuit breaker.

It is another object of the present invention to disclose the motorized tracked vehicle as described above, additionally comprising a controller.

It is another object of the present invention to disclose the motorized tracked vehicle as described above, wherein the controller is configured to display a member of a group consisting of display electrode voltage, load current, soil temperature, soil humidity, soil conductivity, track shoe temperature, electrode temperature, generator overload status, transformer overload status and any combination thereof.

It is another object of the present invention to disclose the motorized tracked vehicle as described above, wherein the controller is configured to provide at least one alert.

It is another object of the present invention to disclose the motorized tracked vehicle as described above, wherein the at least one alert is selected from a group consisting of alert as to the existence of a breakdown, alert as to the nature of the breakdown, alert as to the location in the system of the breakdown, alert of the probability of a breakdown, alert of an overload, alert of an electrical failure, alert of a short, alert of a failure of a power supply, alert of a failure in a transformer and any combination thereof.

It is another object of the present invention to disclose the motorized tracked vehicle as described above, wherein at least one of the following is true:
  a. at least one of said at least two electrodes is configured to be heated to a temperature of at least 200 C;
  b. said soil data is selected from a group consisting of humidity, temperature, conductivity and any combination thereof;
  c. at least two of said linked track shoes have a flexible linkage;

d. said pin-like electrode is reversibly attachable to said track shoe;
e. said motorized tracked vehicle is configured to be operable in a manner selected from a group consisting of manually, autonomously and any combination thereof; and
f. said motorized tracked vehicle is configured to be remotely controllable.

It is another object of the present invention to disclose the motorized tracked vehicle as described above, wherein each of said at least two electrodes is configured to be heated by a method selected from a group consisting of induction heating, resistance heating, electric arc heating, dielectric heating and any combination thereof.

It is another object of the present invention to disclose the motorized tracked vehicle as described above, wherein each of said at least two electrodes is configured to be heated by induction heating.

It is another object of the present invention to disclose the motorized tracked vehicle as described above, wherein a length of said pin-like electrode is 30 cm.

It is another object of the present invention to disclose the motorized tracked vehicle as described above, wherein a length of said pin-like electrode is in a range from 15 cm to 50 cm.

It is another object of the present invention to disclose the motorized tracked vehicle as described above, wherein a diameter of pin-like electrode is 5 cm.

It is another object of the present invention to disclose the motorized tracked vehicle as described above, wherein a diameter of pin-like electrode is in a range from 1 cm to 10 cm.

It is another object of the present invention to disclose the motorized tracked vehicle as described above, wherein a distance between an outer edge of one of said at least two electrodes and an outer edge of an adjacent one of said at least two electrodes is in a range from 1 cm to 15 cm.

It is another object of the present invention to disclose the motorized tracked vehicle as described above, wherein a distance between an outer edge of one of said at least two electrodes and an outer edge of an adjacent one of said at least two electrodes is in a range from 2 cm to 10 cm.

It is another object of the present invention to disclose the motorized tracked vehicle as described above, wherein a distance between an outer edge of one of said at least two electrodes and an outer edge of an adjacent one of said at least two electrodes is in a range from 4 cm to 5 cm.

It is another object of the present invention to disclose the motorized tracked vehicle as described above, wherein the track shoes have a width in a range from 10 cm to 50 cm.

It is another object of the present invention to disclose the motorized tracked vehicle as described above, wherein the track shoes have a width of 20 cm.

It is another object of the present invention to disclose the motorized tracked vehicle as described above, wherein the track shoes have a length in a range from 10 cm to 50 cm.

It is another object of the present invention to disclose the motorized tracked vehicle as described above, wherein the track shoes have a length of 20 cm.

It is another object of the present invention to disclose the motorized tracked vehicle as described above, wherein said power supply comprises at least one generator and at least one power unit.

It is another object of the present invention to disclose the motorized tracked vehicle as described above, wherein said at least one generator generates power at 220 VAC.

It is another object of the present invention to disclose the motorized tracked vehicle as described above, wherein said at least one power unit generates power at a power level of 5000 W.

It is another object of the present invention to disclose the motorized tracked vehicle as described above, wherein said power unit output power is in a range between 2000 W and 10000 W.

It is another object of the present invention to disclose the motorized tracked vehicle as described above, wherein said power unit output power is in a range between 3000 W and 6000 W.

It is another object of the present invention to disclose the motorized tracked vehicle as described above, wherein said power unit output power is 5000 W.

It is another object of the present invention to disclose the motorized tracked vehicle as described above, wherein said motorized tracked vehicle comprises a plurality of rollers.

It is another object of the present invention to disclose the motorized tracked vehicle as described above, wherein said plurality of rollers and said endless tack are configured to form a caterpillar-type tread.

It is another object of the present invention to disclose the motorized tracked vehicle as described above, wherein at least one motor is configured to rotate said at least one roller.

It is another object of the present invention to disclose the motorized tracked vehicle as described above, wherein said motorized tracked vehicle is either self-contained or is configured to be attachable to another vehicle.

It is another object of the present invention to disclose the motorized tracked vehicle as described above, wherein said attachment comprises electrical connectivity via a power take off (PTO).

It is another object of the present invention to disclose the motorized tracked vehicle as described above, wherein said land is selected from land in a group consisting of an open area or an enclosed space.

It is another object of the present invention to disclose the motorized tracked vehicle as described above, wherein said land in an open area is selected from a group consisting of a field, arable land, agricultural land, cropland, pasture, rangeland, grassland, shrubland, a nursery, an orchard, a garden, a lawn, forestry, silviculture, a sport field, cultivable land, a plantation, a berm, a verge, land requiring remediation, and any combination thereof.

It is another object of the present invention to disclose the motorized tracked vehicle as described above, wherein said land requiring remediation is selected from a group consisting of land requiring removal of plant-damaging pathogens, land requiring removal of animal-damaging pathogens, land requiring removal of chemicals and any combination thereof.

It is another object of the present invention to disclose the motorized tracked vehicle as described above, wherein said land in an enclosed space is selected from a group consisting a barn, a greenhouse, a stable, a dovecot, soil for indoor remediation and any combination thereof.

It is another object of the present invention to disclose the motorized tracked vehicle as described above, wherein said soil for indoor remediation is selected from a group consisting of soil from a vertical farming operation, soil from a greenhouse and any combination thereof.

It is another object of the present invention to disclose a method for disinfecting soil, said method comprising steps of
obtaining a motorized tracked vehicle for driving on land comprising:
at least one endless track in mechanical contact with at least one roller, said at least one endless track comprising a plurality of linked track shoes;
at least one sensor for detecting soil data, said sensor mounted on said vehicle;
at least two electrodes mounted on said at least one endless track for administering current and voltage to soil;
a processor for processing soil data collected by said sensor; and
an electrical power source for providing said current and said voltage to said at least two electrodes; and
operating said motorized tracked vehicle;
wherein each of said at least two electrodes is pin-like or spike-like and each track shoe comprises at least one of said soil penetrating pin-like or spike-like electrodes protruding substantially perpendicularly and outwardly from said track shoe, said at least one processor configured to determine from said soil data transmitted by said sensors, a value for each set of applied power selected from a group consisting of voltage, current, power level and any combination thereof required to kill or disable at least one type of pathogen; and to instruct said electrical power source to apply said set of applied power to said at least two electrodes.

It is another object of the present invention to disclose a soil disinfector comprising:
at least one endless track in mechanical contact with at least one roller, said at least one endless track comprising a plurality of linked track shoes;
at least one sensor for detecting soil data, said sensor mounted on said vehicle;
at least one electrode mounted on each of said at least one endless track for administering current and voltage to soil;
a processor for processing soil data collected by said sensor; and
an electrical power source for providing said current and said voltage to said electrode;
wherein said electrode is pin-like or spike-like and each track shoe comprises at least one said soil penetrating pin-like or spike-like electrode protruding substantially perpendicularly and outwardly from said track shoe, said at least one processor configured to determine from said soil data transmitted by said sensors, a value for each set of applied power selected from a group consisting of voltage, current, power level and any combination thereof required to kill or disable at least one type of pathogen; and to instruct said electrical power source to apply said set of applied power to said at least one electrode.

BRIEF DESCRIPTION OF THE FIGURES

In order to better understand the invention and its implementation in practice, a plurality of embodiments will now be described, by way of non-limiting example only, with reference to the accompanying drawings, wherein
FIG. 1 schematically illustrates an embodiment of the system of the present invention.

DETAILED DESCRIPTION OF THE PREFERRED EMBODIMENTS

Figure 1:
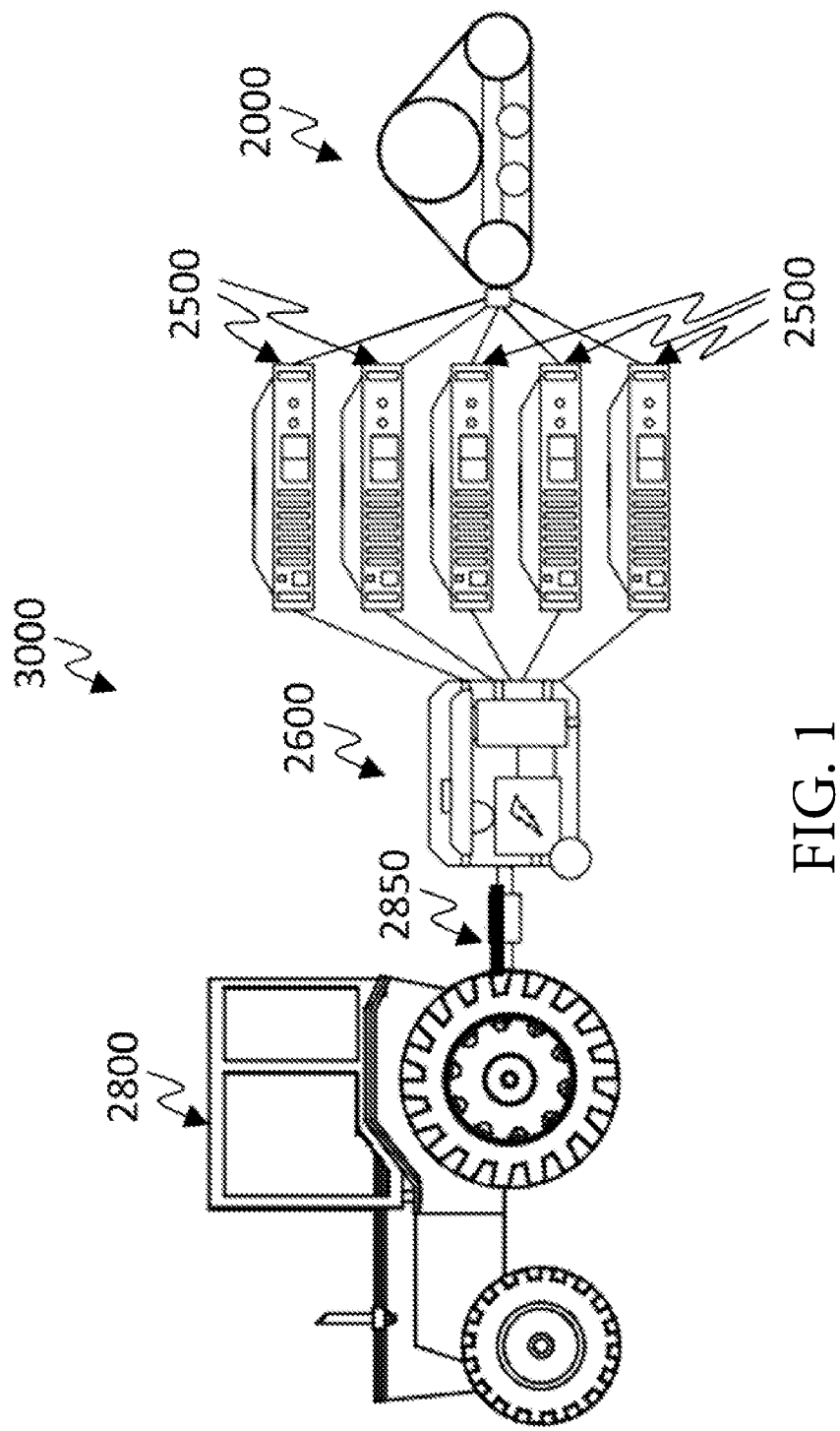

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide a means and method for destroying microorganisms in soil using electric voltage.

A device for disinfection by applying AC current and voltage, DC current and voltage or both AC and DC current and voltage to the soil is disclosed. The current and voltage, AC, DC or both is applied via electrodes inserted into the soil. In some embodiments of the invention the device is a motorized vehicle. In preferred embodiments, rod, spiked or pin-like electrodes are mounted on, and protruding from, a roller of the vehicle so that the area of soil to be disinfected progresses sequentially in direction of the roller as it is moved across the soil. In some embodiments of the invention the aforementioned spiked, rod like or pin like electrodes are so arranged on the roller that they provide grip on the soil surface as the roller moves forward.

In preferred embodiments of the present invention the roller is provided with track shoes, and in other embodiments a plurality of rollers are arranged sequentially in operational contact with the chassis of the aforementioned vehicle. In yet other embodiments the track shoes are linked in an endless track arranged to travel over the aforementioned rollers, in a 'tank-like" configuration.

Soil disinfection can be in an open area or in an enclosed space. The open area can be, but is not limited to, a field, arable land, agricultural land, cropland, pasture, rangeland, grassland, shrubland, a nursery, an orchard, a garden, a lawn, forestry, silviculture, a sport field, cultivable land, a plantation, a berm, a verge, land requiring remediation, and any combination thereof. The remediation can be to remove plant-damaging pathogens, animal-damaging pathogens, chemicals and any combination thereof. The enclosed space can be inside a barn, a greenhouse, a stable, a dovecot, and any combination thereof. Soil requiring remediation can also be treated in an indoor setting. For non-limiting example, soil from a vertical farming operation or from a greenhouse can be transferred to a treatment center where the soil is disinfected. Such treatment can be carried out indoors to prevent accidental spreading of the pathogen.

Greenhouse disinfection can be via electrodes mounted on track shoes attached to at least one roller or via electrodes mounted on a stationary support, where the stationary support can be movable, but not while the electrodes are embodied in soil. Preferably, the stationary support can be raised and lowered so that the electrodes can be inserted into or removed from the earth in the greenhouse. In some embodiments, the stationary support is of a shape and size such that the electrodes can be reversibly lowered into earth beds within a greenhouse. In some embodiments, the electrodes being not in contact with the earth, the stationary support can be moved from one portion of a greenhouse to another or from one earth bed to another.

The distance between the electrodes can be optimized in accordance with the type of soil to be disinfected.

The electrodes have a generally similar cross-section from their proximal end, adjacent to the base of the track shoe, to their distal end, furthest away from the base of the track shoe. The electrodes do not need a horizontal extension in any part of the electrode body or at their distal end. For non-limiting example, the pin-like electrodes can be cone-shaped, spike shaped, truncated cone shaped, cylindrical, sharp at the end, or knife-shaped.

FIG. 1 schematically illustrates an embodiment (3000) of the present system. In an embodiment of this type, a tractor (2800) comprising a power take off (PTO) (2850) is electrically connected via the PTO to a generator (2600). The generator (2600) is in electrical communication with a plurality of power supplies (2500); in the schematic illustration of FIG. 1, for clarity, only five of the power supplies (2500) are shown. The power supplies (2500) are voltage and current stabilized and also function as transformers, with their output voltage larger than their input voltage. The power supplies (2500) are in electrical communication with the disinfection unit.

The system can be pullable by a tractor, as illustrated in FIG. 1, or it can be self-contained. If self-contained, it can be operable autonomously or by remote control.

The disinfection unit, as discussed below, can comprise a motor to propel the disinfection unit, the disinfection unit can lack a motor and be movable by the tractor or by another external motive power, or the disinfection unit can be stationary, for example, a disinfection unit for a fixed site such as, but not limited to, an interior of a building such as a barn or greenhouse.

The system comprises at least one sensor (1900) to measure at least one of the humidity of the soil, the conductivity of the soil and the temperature of the soil; at least one power generator configured to generate power at a predetermined current and voltage, a processor to control the current and voltage generated by at least one power generator, the values of the current and voltage depending on the measured parameters; and a set of electrodes to deliver the power at the current, voltage and power values determined by the processor. For example, dry soil, which typically has a high resistance, will require a higher current for disinfection than a soil, such as a wet soil, with a lower resistance.

Figure 2:
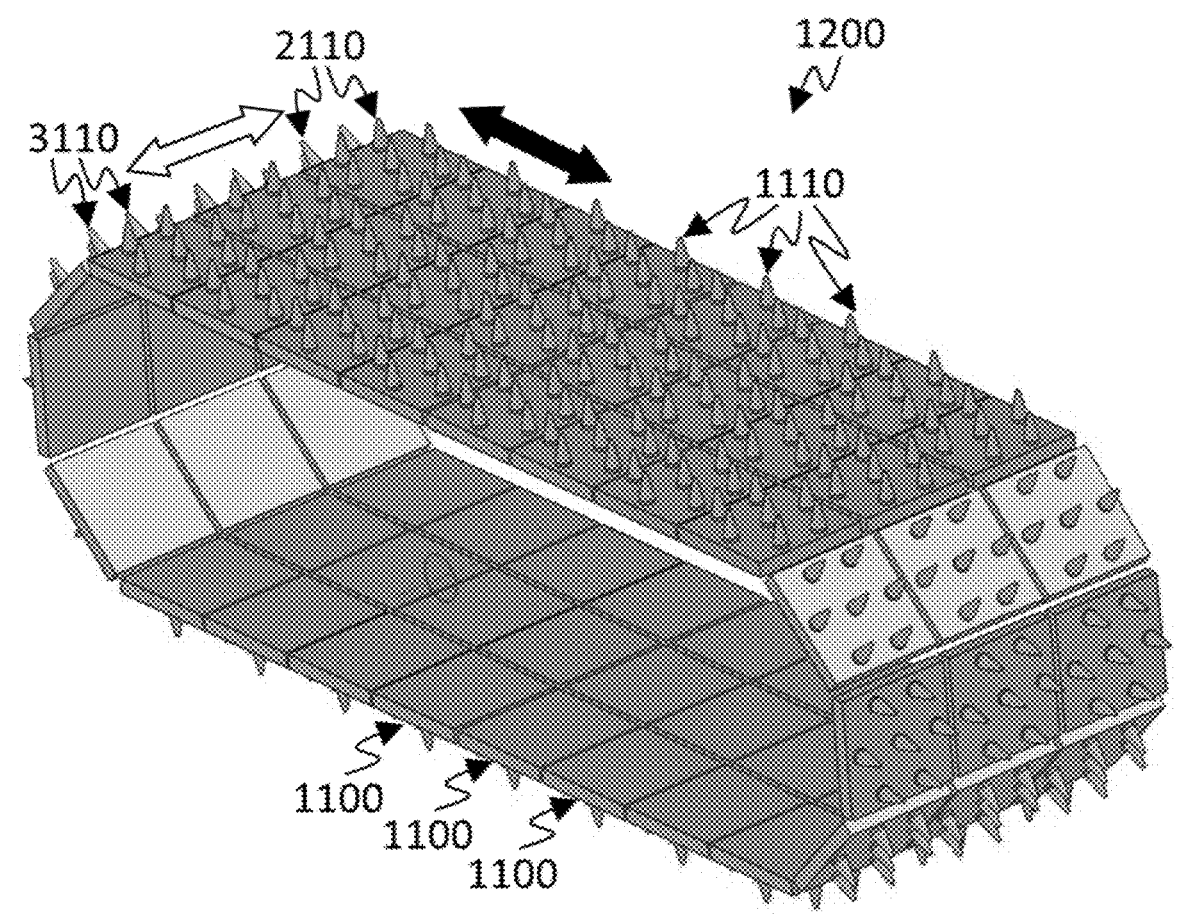
FIG. 2 schematically illustrates an embodiment of an endless track comprising a plurality of linked-together track shoes, each track shoe comprising a plurality of electrodes.

As shown in FIG. 2, the disinfection unit typically comprises an endless track (1200). In this embodiment, the track comprises a plurality of track shoes (1100). Typically, the track shoes (1100) are flexibly linked to each other, at least in a longitudinal direction (black arrow) and preferably also in a transverse direction (white arrow) so that the angle between adjacent track shoes (1100) can change as the endless track (1200) rotates.

Figure 3:
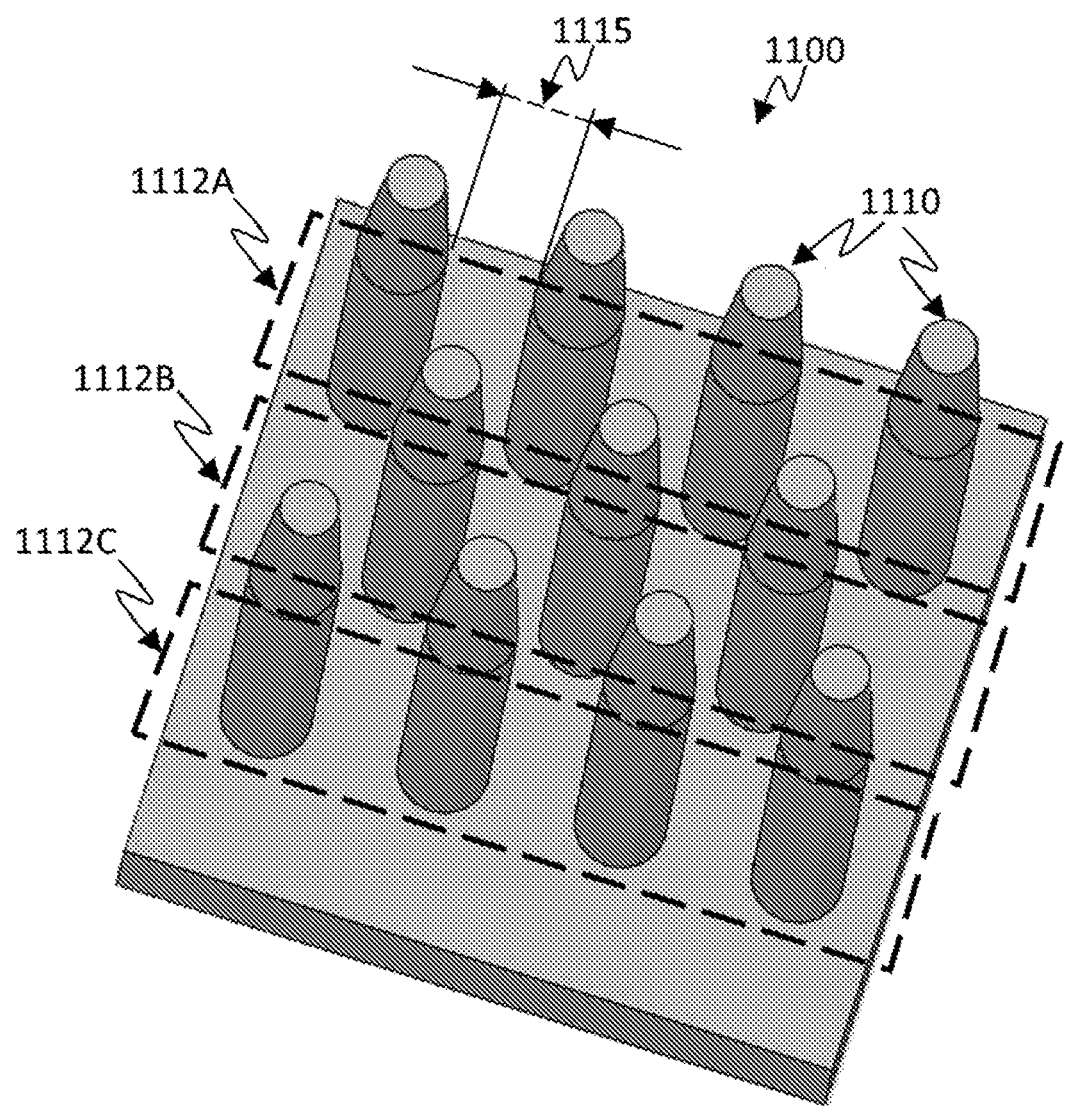
FIG. 3 schematically illustrates an embodiment of a track shoe and electrodes.

As shown in FIG. 3, each track shoe (1100) comprises at least one electrode (1110) and preferably a plurality of electrodes (1110). Preferably, each electrode (1110) is attached at its distal end to the track shoe (1100). Typically, to each track shoe (1100) is attached a plurality of electrodes (1110) arranged in rows (1112A, 1112B, 1112C), the rows preferably staggered to ensure complete coverage of the soil by the power.

Electrodes (1110) are typically about 30 cm long, and the electrode length can be in a range from 15 cm to 50 cm.

The diameter of the electrodes (1110) at their distal end is typically about 5 cm, with the diameter depending on, among other things, the strength of the electrode material. The electrodes (1110) need to be strong enough not to bend or break when inserted into or removed from hardened soils. Electrodes (1110) are typically of hardened steel or any electrically conductive material which is resistant to, among other properties, abrasion and fracture.

The edge-to-edge distance (1112) (open space) between the electrodes (1110) is preferably between 1 cm and 15 cm, more preferably between 2 cm and 10 cm and still more preferably about 4 cm to 5 cm.

The track shoes (1100) are typically approximately square, being about 20 cm by about 20 cm, but can vary in width from about 10 cm to about 50 cm and vary in length from about 10 cm to about 1 m.

Preferably, the electrodes (1110) are reversibly attached to the track shoes (1200), so that a damaged or otherwise unsatisfactory electrode (1110) can be replaced.

The endless track (1200) is typically mounted on at least one roller that enables the endless track (1200) to move around the periphery of a single roller or around a track defined by the outer edges of a set of rollers.

Figure 4:
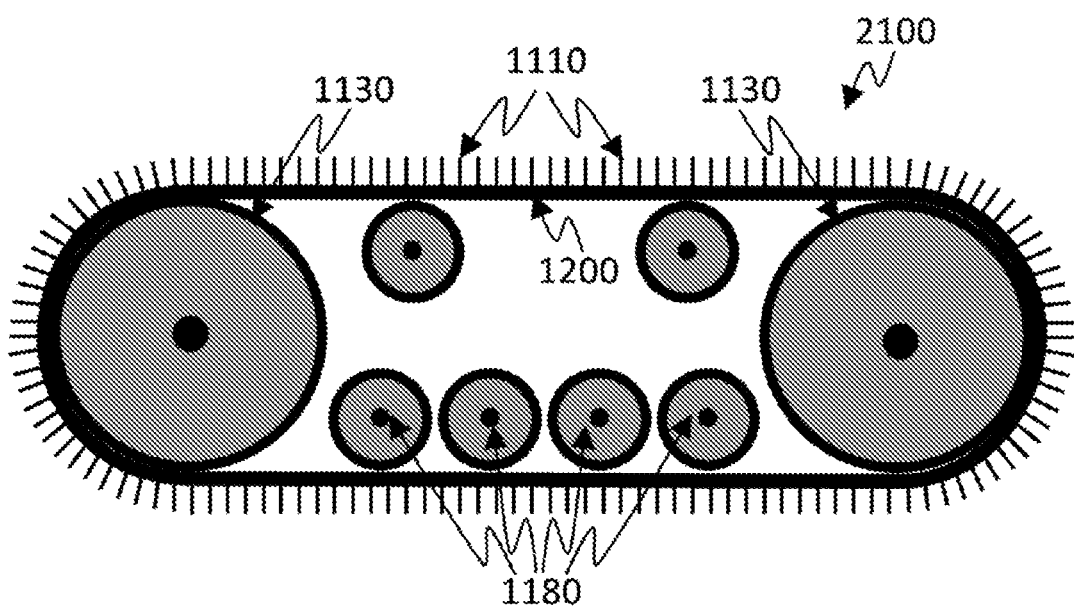
FIG. 4 schematically illustrates an endless belt forming a caterpillar tread.

FIG. 4 shows an exemplary schematic illustration of an embodiment (2100) wherein the endless track (1200) is a caterpillar-type tread mounted on a plurality of rollers (1130, 1180). In such a caterpillar-type embodiment, large rollers (1130) support the weight of the device and small rollers (1180) control vertical displacement the endless track between the large rollers (1130) and provide motive power to drive the endless track (1200). For simplicity, the electrodes (1110) are schematically indicated, but the individual track shoes and the joints between the track shoes are not shown.

Figure 5:
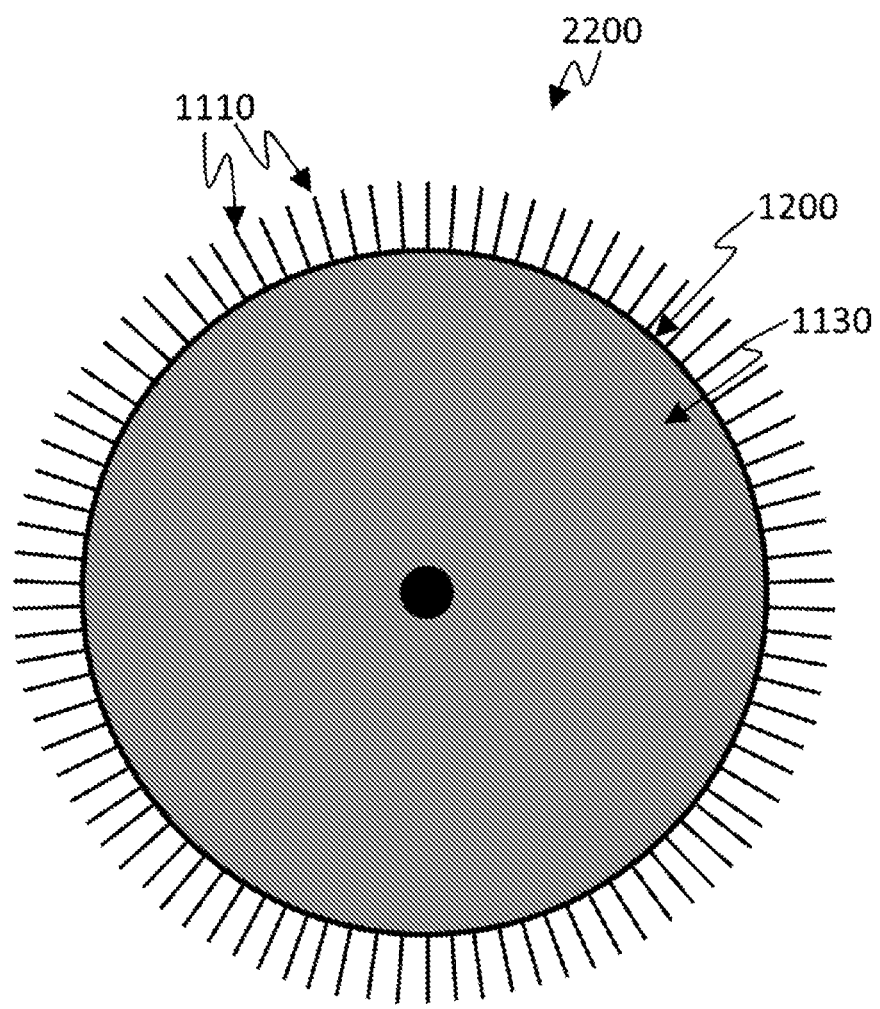
FIG. 5 schematically illustrates an endless belt on a single roller.

FIG. 5 shows an exemplary schematic illustration of an embodiment (2200) where the endless track (1200) is mounted on a single roller (1130). For simplicity, the electrodes (1110) are schematically indicated, but the individual track shoes and the joints between the track shoes are not shown.

In preferred embodiments, the system further comprises a means to enable the system to traverse ground with the electrodes not touching the ground. Typically, such an embodiment comprises a secondary set of wheels without electrodes and a means to either raise the rollers and endless track or to lower the secondary wheels so that the electrodes do not contact the ground.

The at least one roller can be unpowered, with its rotation induced by forward motion of the system, or the at least one roller can be powered, with the forward movement of the system at least partly induced by the power applied to the endless track (1200).

In use, the portions of the endless track (1200) in contact with the soil are stationary; as the endless track (1200) moves forward, the electrodes (1110) in the rear-most of the track shoes (1100) in contact with the soil are pulled out of the soil and the electrodes (1110) of a row of track shoes (1100) that is immediately in front of the front-most set of track shoes (1200) currently in the soil is pushed into the soil.

The endless track (1200) is typically about 6 m long and about 1.2 m wide. The length can be in a range from 3 m to 15 m, and the width can be in a range from 50 cm to 3 m. Preferably, the endless track (1200) is at least as wide as the at least one roller.

The endless track and, preferably, the at least one roller should have a very high mechanical resistance, to avoid breakage or damage during use, and a resistance to harsh surface conditions such as roughness of soil, humidity, and extreme temperatures. (Outdoor soil temperature can vary between about −20 C and about 50 C; more typically, the system can be operating at a temperature between about 0 C and about 40 C).

Typically, the disinfection unit has at least two endless tracks, at least one with positive polarity see FIG. 2, front row electrodes 2110) and at least one with negative polarity (see FIG. 2, rear row electrodes 3110). In some embodiments, at least one longitudinal join between two rows of track shoes is insulating so that at least one longitudinal section comprising the entire length of the endless track has positive polarity while at least one other longitudinal section of the endless track, also comprising the entire length of the endless track, has negative polarity.

The generator electrically connected to the tractor's PTO is configured to generate about 20,000 W to 60,000 W, preferably 30,000 W to 50,000 W, more preferably about 50,000 W, at about 220 VAC. The power from the generator is preferably voltage stabilized and current stabilized, with the stabilization controlled by a motor rotary controller.

In these embodiments, the system further comprises at least one power supply and transformer, configured to output power at about 3000 V, with the output of the generator being in a range from about 800V to about 10,000V.

In preferred embodiments, the power generated by the generators is distributed to five power supplies, the power supplies being voltage and current stabilized. The power supplies are controlled according to the soil conditions, such as, but not limited to, the soil humidity and conductivity, with the current and voltage output by the power supplies being alterable to ensure consistent disinfection of the soil for a wide range of soil conditions.

The processor is configured to input at least one signal from at least one sensor and, in some embodiments, to input other data such as, but not limited to, the speed of the tractor and at least one command from a control unit in the tractor, and to determine from the at least one sensor signal and, if present, at least one other datum, to output to the generator, the transformer, and any combination thereof, the current, voltage and power to be applied to the at least two electrodes.

The processor is further configured to execute at least one set of instructions, the instruction set comprising at least one instruction for controlling a treatment of a portion of soil. The instruction(s) is selected from a group consisting of: a startup instruction for bringing the system from an inactive state (no power to the electrodes, room temperature electrodes, no power to a unit propelling the system forward, etc.) to an active state (at least one of power at predetermined voltage, current and power level, electrode at a predetermined temperature, soil at a predetermined temperature and predetermined power or speed to a unit propelling the system forward), maintain a predetermined active state for a predetermined time, maintain a predetermined active state for a predetermined distance, change the active state to another active state, and bring the system from an active state to an inactive state.

An instruction set can be accepted from the controller in the cab or can be stored in a database. It should be noted that an instruction can be "execute a given instruction set, as stored in the database".

In preferred embodiments, all control data are displayed by the controller, enabling the user to remain in full control of the system.

In preferred variants of embodiments with more than one power unit, the controller is further configured to determine which power unit(s) are used to supply power to the electrodes and the amount of power supplied by each unit, all of the power unit parameters being changeable depending on the total power required at any given time and the operating characteristics of each power unit, such as, but not limited to, the maximum power (power level, current and voltage) supplyable by the power unit(s), the fraction of maximum power (power level, current and voltage) being utilized, the temperature of the power unit(s) and any combination thereof.

In some embodiments, the system comprises a controller configured to be mounted within the tractor cab, the controller configured to display electrode voltage, load current, soil temperature, soil humidity, soil conductivity, track shoe temperature, electrode temperature, generator overload status, transformer overload status and any combination thereof. The controller is further configured to accept use input of electrode voltage, load current, power and any combination thereof to be applied to the electrodes; to activate and deactivate the system, to clear a generator overload status, to clear a transformer overload status, and any combination thereof. In some embodiments, the controller is further configured to automatically perform: setting an electrode voltage, setting a load current, setting power and any combination thereof to be applied to the electrodes; activating and deactivating the system, clearing a generator overload status, clearing a transformer overload status, and any combination thereof.

In some embodiments, the system is configured as a self-contained unit. In such embodiments, the system does not require a tractor or other motive power, all motive power being applied by means of the endless track. In some variants of such embodiments, the system is controllable by a user, with commands and other input to the system and alerts, warning, conditions and other system output being received from and delivered to a user as described above. In some variants of such embodiments, the system is autonomous, a set of instructions being provided which sets the parameters of the disinfection treatment and the area to be disinfected, with the system thereafter acting autonomously without further user input. In some variants of autonomous systems, alerts can be provided in case of breakdown, a serious fault, an emergency, and any combination thereof.

Power Unit

The power unit comprises at least one generator and at least one power supply.

The generator(s) are configured to supply at least 20,000 W, preferably 50,000 W, and, in some embodiments, 60,000 W of total power at 220 VAC.

In some embodiments, the power unit comprises a plurality of power supplies, each power supply configured to deliver 5000 W at 220 VAC.

The power supply(s) can be a part of the tractor, a stand-alone power supply and any combination thereof.

Any generator can have input from a tractor power supply, a stand-alone power supply and any combination thereof.

Preferably, a stand-alone power supply will be towable by the tractor, although some embodiments can have at least one generator in electrical communication with at least one of an independently movable power supply, a power supply towed by an independently movable unit (such as, but not limited to, another tractor), and a stationary power supply.

Preferably, the generator(s) are pulled by the same tractor as pulls the disinfection unit. However, in less-preferred embodiments, at least one generator can be independently movable, towed by an independently movable unit (such as, but not limited to, another tractor), and stationary.

The processor can be further configured to determine the speed of the system, either by inputting the speed of the tractor and setting the forward speed of the system to equal that of the tractor, or vice versa.

The processor can be further configured to determine the presence of a mechanical breakdown in at least part of the system. In such embodiments, the processor can perform at least one of: alert the user as to the existence of a breakdown, alert the user as to the nature of the breakdown, alert the user as to the location in the system of the breakdown, and put at least part of the system in an inactive state, In some embodiments, based on sensor input, length of time in use, etc., the processor can be further configured to provide an alert of the probability of a breakdown.

In preferred embodiments, the endless track and at least one roller can be raised or lowered, for non-limiting example, by means of an integral hydraulic, mechanical or pneumatic system, thus enabling the system to be moved without the electrodes contacting the ground.

In preferred embodiments, the system comprises at least one circuit breakers for the system. Alternatively or additionally, individual power supplies can have a circuit breaker, as can the transformer and the endless track.

Figure 6:
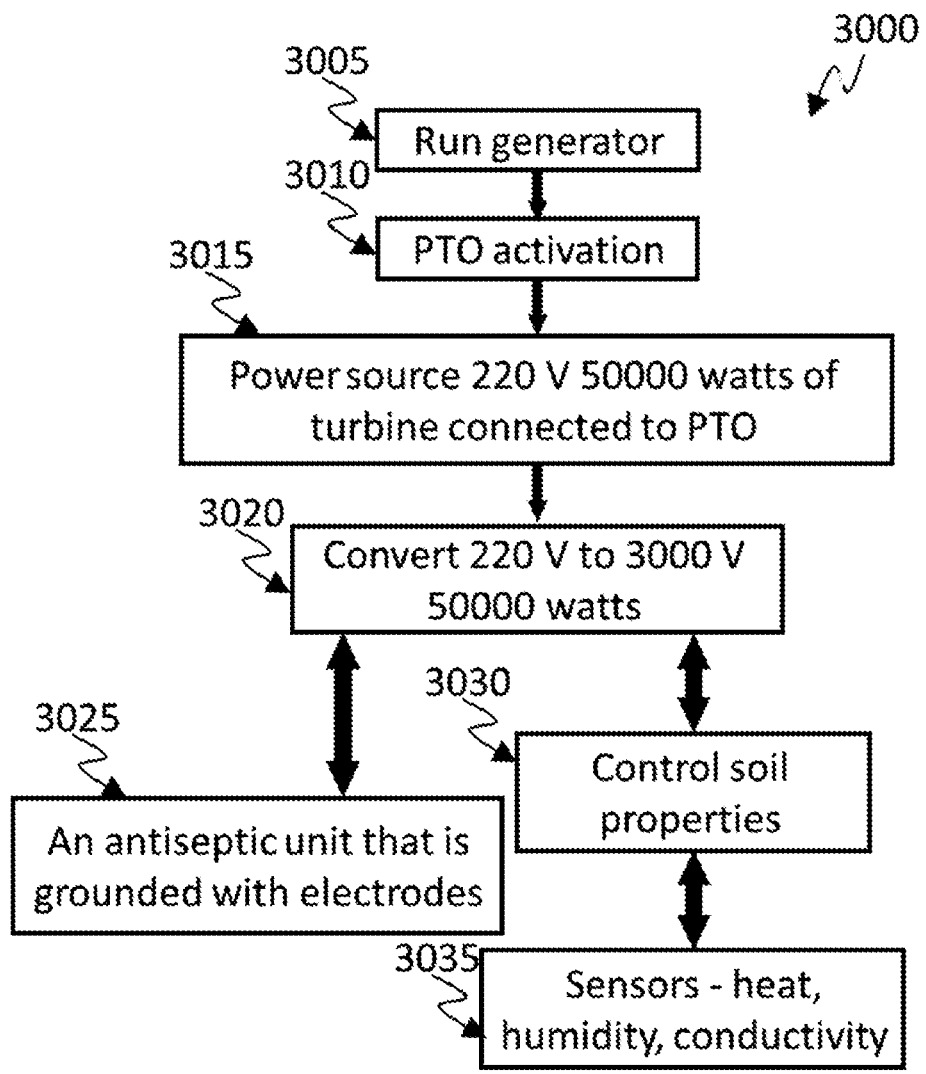
FIG. 6 illustrates an embodiment of a soil disinfection flow chart.

An illustrative embodiment of a flow chart (3000) for a soil disinfection unit is shown in FIG. 6. When the system is activated, the generator is started (3005) and the PTO is activated (3010) so that the generator (power source) can deliver (3015) 50,000 W of power at 220 VAC to the electrodes. The power supply(s) convert (3020) the 220 VAC to approximately 3000 VAC at 50,000 W. The processor inputs (3030) the soil properties as measured by the sensor(s) (3035) and calculates the voltage needed for disinfection. This voltage is then sent to the conversion unit (3020), which then applies it (3025) to the electrodes of the endless track in the antiseptic unit of the system.

In some embodiments, the electrodes can be heated to a temperature of at least 200 C. Typically, the electrodes are heated by induction heating, but any conventional heating means known in the art can be used, for non-limiting example, resistance heating, electric arc heating, and dielectric heating. Any combination of heating means can be used.

Figure 7:
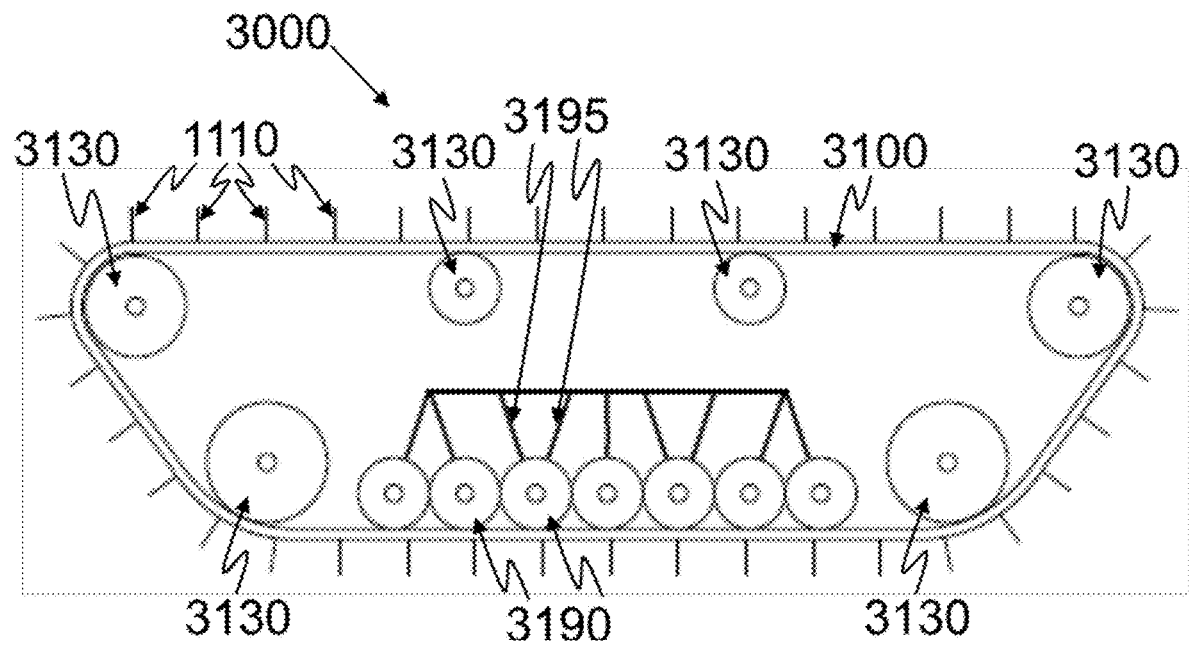
FIG. 7 schematically illustrates another embodiment, with an endless belt supporting rows of electrodes and rollers and plates to conduct the current and voltage from a generator to the electrodes.

FIG. 7 shows another embodiment (3000) of the system of the present invention with an endless track. In this embodiment, the endless track comprises an endless belt (3100) of a flexible or semi-flexible material, movable by means of propulsion rollers (3130). Mounted in the belt (3100) and extending outward are electrodes (1110); the electrodes (1110) pass through the endless belt (3100) so that the tops of the electrodes (1110) can make electrical contact with the power rollers (3190). As in the embodiment shown in FIGS. 2 and 3 above, there are a plurality of rows of electrodes (1110), preferably an even number of rows. Electrodes (1110) in adjacent rows can be staggered, as shown in FIGS. 2 and 3, above, or can be aligned.

The power rollers (3190) are in electrical connection with power supplies (2500, not shown, see FIG. 1, above) and a generator (2600, not shown, see FIG. 1, above), as disclosed above, by means of two sets of tensioner pulleys (3195), one set having positive polarity and feeding the positive contact plates (3120, see FIG. 8) and positive electrodes (3110), the other having negative polarity and feeding the negative contact plates (2120, see FIG. 9) and negative electrodes (2110, behind positive electrodes 3110, see FIG. 2).

The endless belt (3100) can comprise rubber, a flexible or semi-flexible polymer, metal for reinforcement and any combination thereof. The endless belt (3100) is insulating so that virtually no current passes through it.

Figure 8:
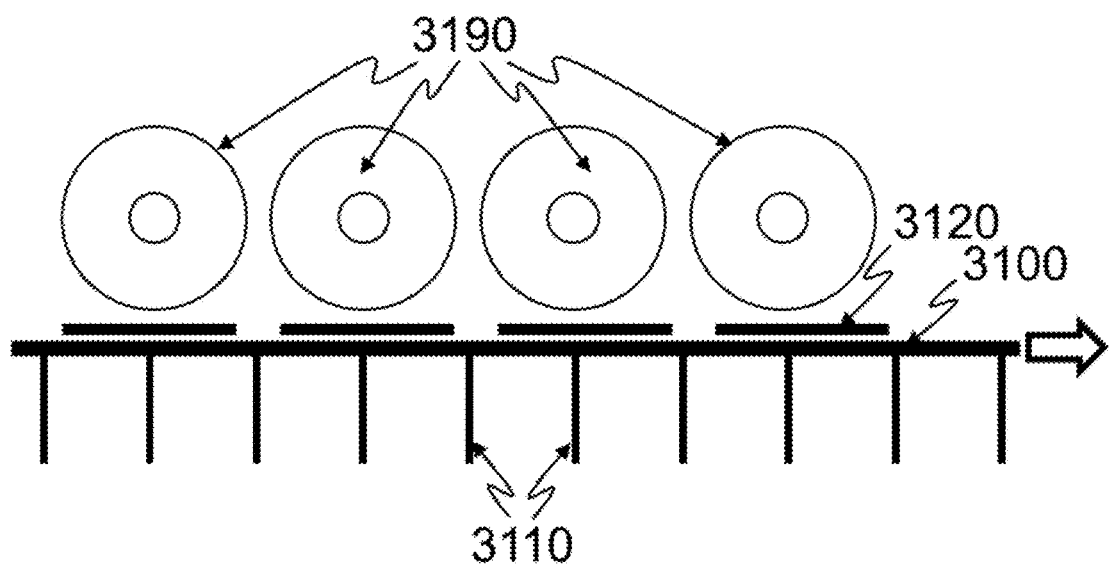
FIG. 8 schematically illustrates the rollers, plates, endless belt and electrodes of the embodiment of FIG. 7.

FIG. 8 schematically illustrates an embodiment of a means of transferring the electrical current and voltage from the power supplies (2500, not shown, see FIG. 1, above) and a generator (2600, not shown, see FIG. 1, above) to the ground. For clarity, the parts are shown separate; in practice, they are in contact during use. The power rollers (3190) are in contact with stationary contact plates (3120) to improve contact between the power rollers (3190) and the electrodes. Passing through the endless belt (3100) and mounted to it are electrodes (3110). The endless belt (3100) moves (white arrow) when driven by the propulsion rollers (3130) and therefore moves the electrodes (2110 (not shown), 3110) under the contact plates (2120 (not shown), 3120). An electrode (2110 (not shown), 3110) under a contact plate (2120 (not shown), 3120) will conduct current and voltage into the ground, thereby sterilizing it.

At least a portion of the surface of the power rollers (3190) comprises metal or other conductive material, so that the power rollers (3190) conduct electricity from the power supplies (2500, not shown, see FIG. 1, above) and a generator (2600, not shown, see FIG. 1, above) to the contact plates (3120), which comprise conductive material. In preferred embodiments, the power rollers (3190) and the contact plates (3120) predominantly comprise a conductive metal, typically iron or steel, although any conductive metal can be used.

The electrodes (1110) comprise conductive material, as disclosed above.

Figure 9:
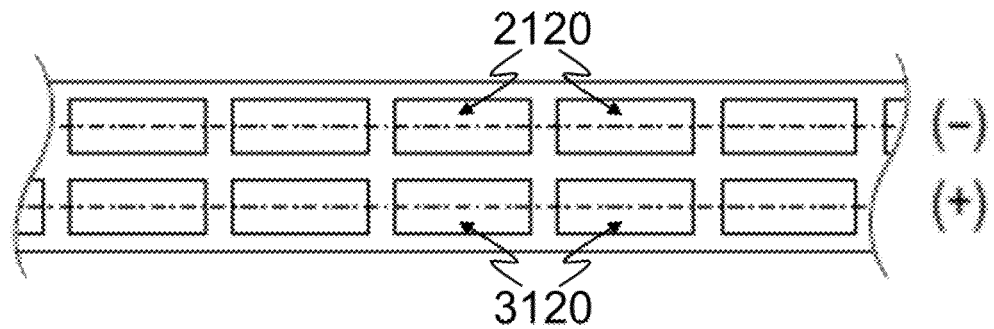
FIG. 9 schematically illustrates two of the rows of plates of the embodiment of FIG. 7.

FIG. 9 schematically illustrates a portion of two rows of contact plates (2120, 3120). As shown in FIG. 9, alternate rows of contact plates have opposite polarity, so current will flow from one row of contact plates (3120) through the electrodes (1110) to at least one adjacent row of contact plates (2120).

In preferred embodiments, there is one row of contact plates (2120, 3120) and one row of power rollers (3190) per row of electrodes. In other embodiments, more than one row of electrodes (2110, 2120) can be powered by a row of contact plates (2120, 3120).

Figure 10:
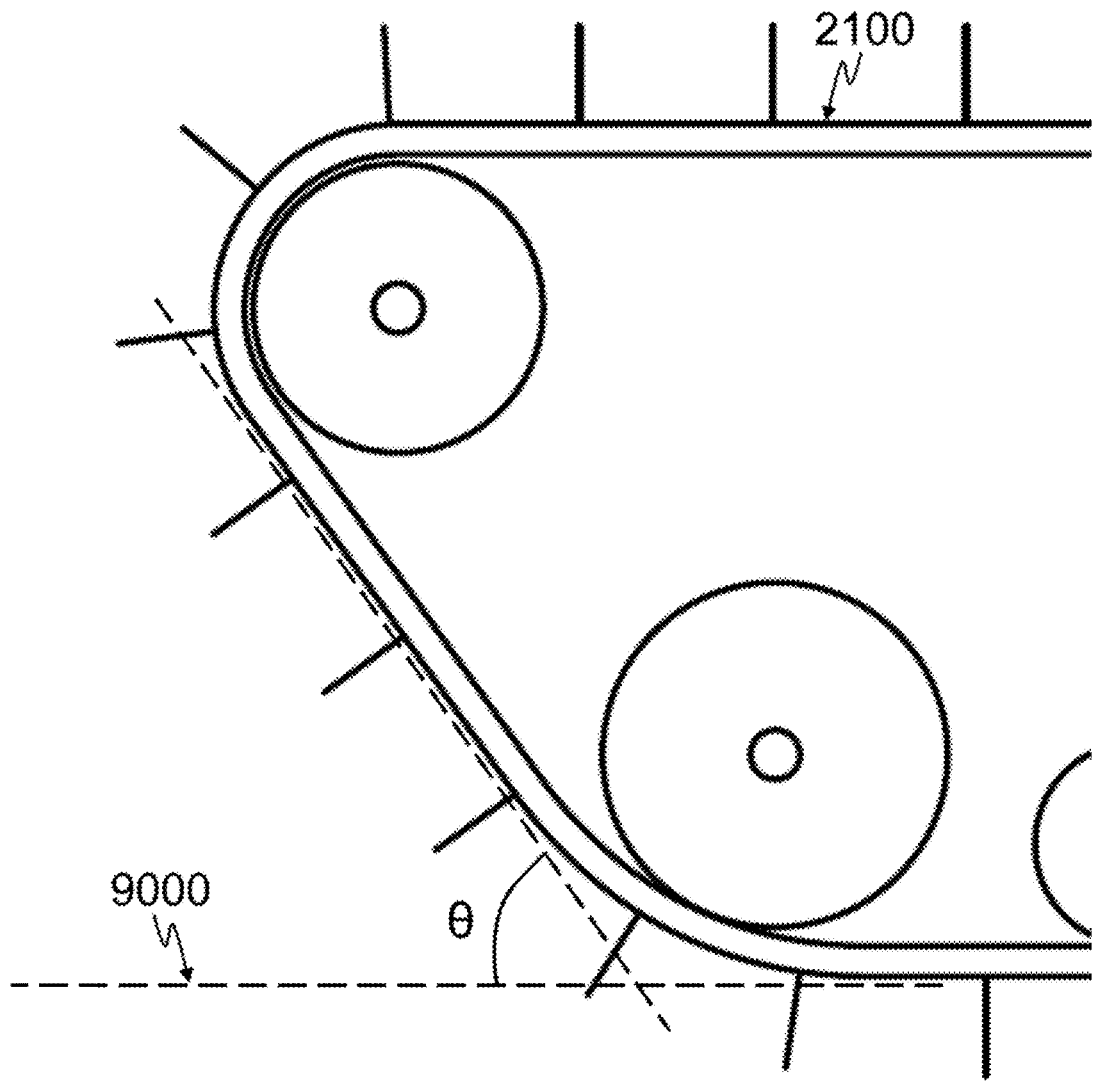
FIG. 10 schematically illustrates the maximum angle between the endless belt and the soil for safe entry of the electrodes into the soil.

As schematically illustrated in FIG. 10, the disinfection unit is configured so that the angle θ between the endless belt (3100) and the ground (9000) is less than 30°. This helps prevent damage to the electrodes by hard or stony ground.

In preferred embodiments, the rows of electrodes are 8 cm apart; the distance between rows of electrodes can be in a range from 3 cm to 30 cm.

In preferred embodiments, an electrode and a next trailing electrode are 8 cm apart; the distance between an electrode and a next railing electrode can be in a range from 3 cm to 30 cm.

In preferred embodiments, the width of the endless belt is 160 cm. The width of the endless belt can be in a range from 50 cm to 800 cm.

A contact plate can be between 3 cm and 60 cm wide, and between 3 cm and 90 cm long.

A power roller can be between 3 cm and 60 cm wide.

Electrification of the soil by an electrode (1110) will start when the electrode (1110) passes under the front edge of the frontmost of the contact plates (3120) and electrification by that electrode (1110) ends when it passes out from under the rearmost of the contact plates (3120). The time each of the electrodes (1110) is in the ground depends on the speed of the tractor and the length of the row of contact plates (3120) under which the electrode (1110) passes. Typically, the time each electrode (1110) is in the ground and is electrifying the ground is between 5 s and 60 s.

The electrode (1110) typically enters the ground before it contacts a contact plate (3120). Typically, electrification starts when an electrode (1110) has been in contact with the ground for about 15 s.

Typically, voltages and currents will be in the ranges disclosed above.

Figure 11:
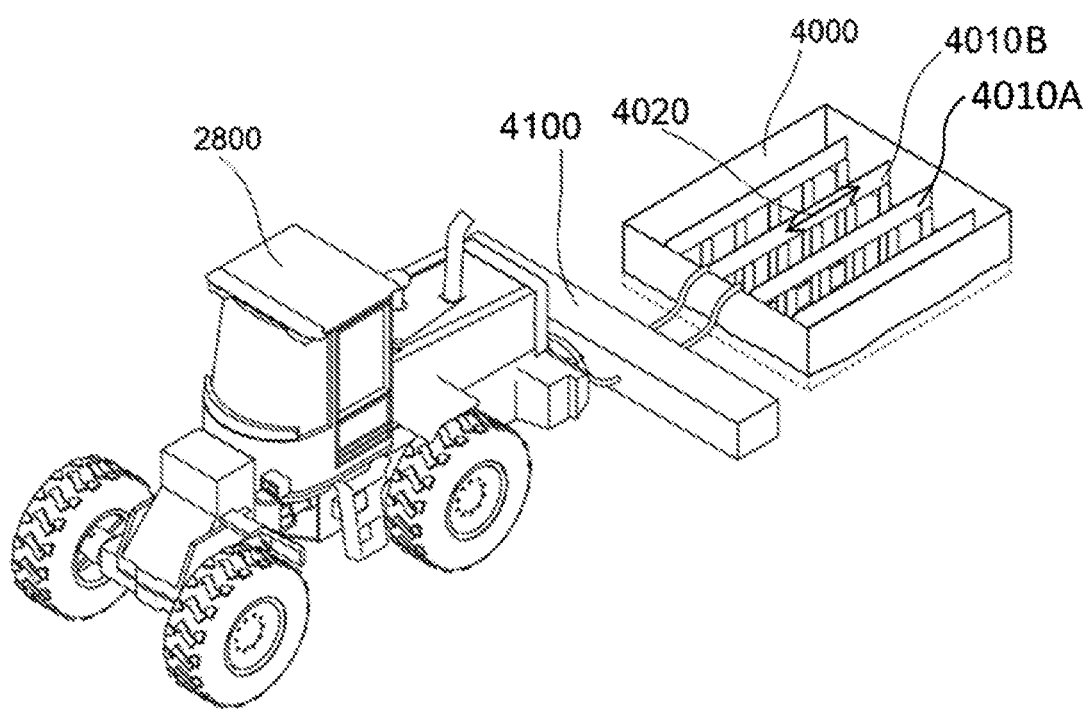
FIG. 11 is an overall view of a trailed implement for electrically disinfecting a soil.

FIG. 11 shows an overall view of an implement comprising an alternative embodiment of the present invention. A tractor (2800) trails a cultivator (4100) configured for stirring and pulverizing soil, followed by implement (4000) of the present invention. The aforesaid implement comprises a plurality of frame electrodes (4010A, B) which are connected to the power supply unit (2500 not shown, see FIG. 1, above) such that the nonboring frame electrodes have opposite polarity. AC and DC power supply units are in the scope of the present invention. At least one of the frame electrodes (4010B) is reciprocally movable along the trailing direction (4020). The mechanical drive and the electrical wires are not shown. In some embodiments, at least one of the frame electrodes (4010A) is fixed to the implement (4000) and is not reciprocally movable. In some embodiments, all the frame electrodes (4010B) are reciprocally movable.

Figure 12:
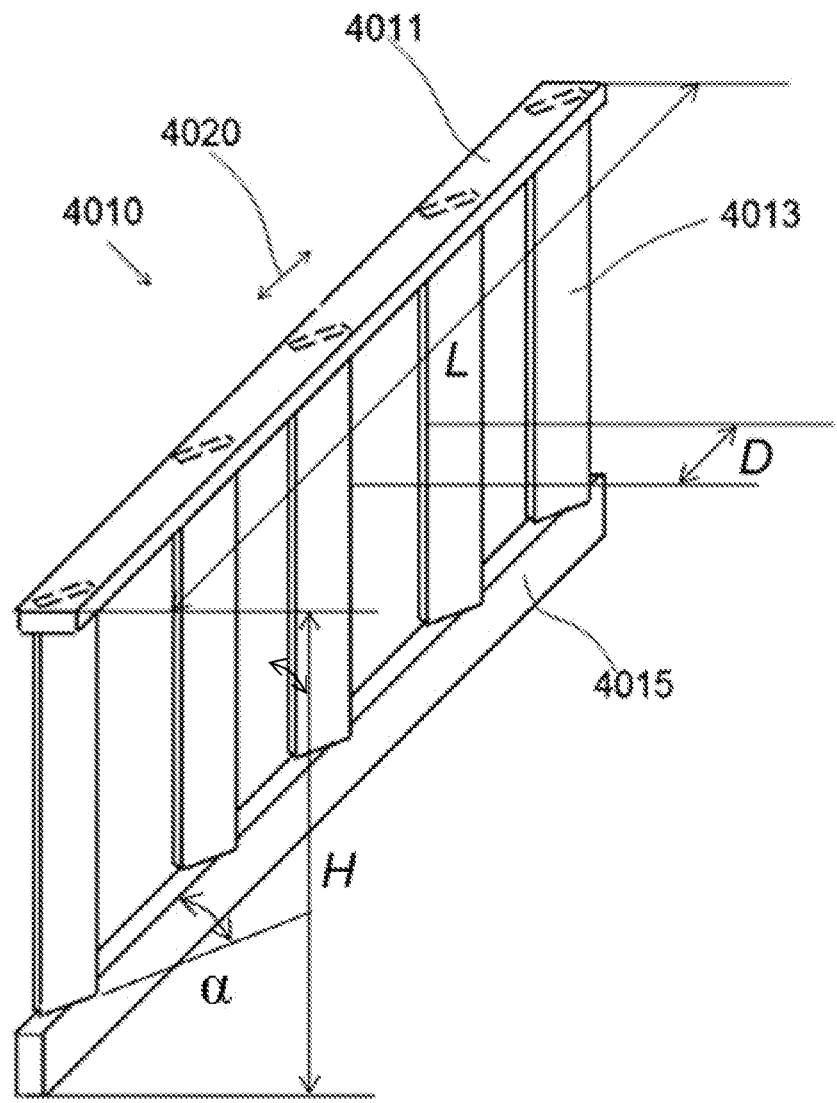
FIG. 12 is an enlarged view of a frame-shaped electrode.

FIG. 12 presents an enlarged view of a frame electrode (4010A, B), which is formed by a top bar (4011), a bottom bar (4015) and a plurality of plate-like plow members (4013). According to an exemplary embodiment, all elements (4011), (4013) and (4015) are secured to each other by welding. The plate-like plow members (4013) are tilted relative to the trailing direction (4020) at angle α ranging between 5 and 90°. Distance D between the plate-like plow members (4013) within said frame-shaped electrode ranges between 4 and 10 cm.

The reciprocally movable frame electrode(s) (4010B) is configured so that the path of the current from the plow members (4013) on the reciprocally movable frame electrode(s) (4010B) to plow members (4013) on an adjacent frame electrode (4010A, B) will vary as the reciprocally movable frame electrode(s) (4010B) moves relative to the adjacent frame electrode (4010A, B). For non-limiting example, when a reciprocally movable frame electrode (4010B) is at the front of its travel, current will travel from a first plow member (4013) on the reciprocally movable frame electrode (4010B) to a first plow member (4013) on the adjacent frame electrode (4010A, B), second to second, and so on. When the reciprocally movable frame electrode (4010B) is at the back of its travel, current will travel from a first plow member (4013) on the reciprocally movable frame electrode (4010B) to a second plow member (4013) on the adjacent frame electrode (4010A, B), second to third, and so on. In this manner, the paths of the current through the soil will vary in direction as the implement (4000) moves through the soil, improving the evenness of the coverage of the sterilizing current in the soil.

Typically, the currents and voltages employed will be in the ranges disclosed above.

Example 1

The efficacy of treatment for killing nematode species has been examined, since nematodes are a key detrimental factor for many commonly-grown crops, such as, but not limited to, citrus trees, bananas, barley, beans, lettuce, potatoes, melons, strawberries and tomatoes.

Initial experiments, as shown in Table 1, have indicated current and voltage levels needed to reliably kill nematodes.

Soil moisture and soil temperature were measured before and after the treatments to maximize the efficiency of the disinfection process. Soil preparation was the same for the five experiments.

It can be seen that, to kill nematodes, at least 1000 V is needed at a current above about 4.6 A. The optimum exposure time is 4 separate exposures, each of about 10 s.

TABLE 1

Effectiveness of different currents, voltages and exposure times on killing nematodes in soil

| Results | | Treatment | | | |
|---|---|---|---|---|---|
| Disinfection Effectiveness | Effect | Current (A) | Exposure Time (s) | Voltage (V) | No. |
| 5% | No effect | 0.18 | 15 | 220 | 1 |
| 23% | Some disinfection. Not uniform | 0.23 | 15 | 220 | 2 |
| 76% | Good disinfection. Not uniform | 2.85 | 4 × 10 | 1000 | 3 |
| 84% | Good disinfection. | 4.6 | 2 × 20 | 1000 | 4 |
| 96% | Excellent disinfection. | 7.64 | 4 × 10 | 1000 | 5 |

Example 2

The effect of different exposure times on growth of plants was studied.

Figure 13A:
FIG. 13A-C depicts the effect of applying electric power on the growth of plants.
Figure 13B:
Figure 13C:

FIG. 13A-C shows the results of the growth tests. The plants were planted in soil that contained a predetermined concentration of nematodes, one known to be sufficient to inhibit growth of the plants.

FIG. 13A shows the growth of the control plants, which had no exposure to current or voltage. FIG. 13B shows the growth of plants which had a short exposure to a predetermined current and voltage at a predetermined power, the voltage, current and power chosen to be effective at killing nematodes. FIG. 13C shows the growth of plants which had a long exposure to the same predetermined current and voltage as the plants of FIG. 13B.

The control plants of FIG. 13A, which received no exposure to the electric power. The control plants were found to be delayed, with sparse leaves and a smooth and undeveloped root system. They are the smallest, have the fewest leaves and have the least root development. The plants of FIG. 13B, which had a short exposure, show considerably more root development than the plants of FIG. 13A. The plants of FIG. 13B are larger and have more leaves. The plants of FIG. 13C, which had a long exposure, show nearly twice as much root development as the plants of FIG. 13B. the plants of FIG. 13C are significantly larger than those of FIG. 13B, have significantly more leaves and appear more mature than the plants of FIG. 13B, with those plants appearing more mature than the plants of FIG. 13A.

Example 3

The effect of different exposure times on disinfection of different types of soil was studied.

It is well known that soils can have different moisture content at different times and that different types of soil hold moisture in different ways. Since water is a conductor, the resistance of the soil will depend on the soil type and the soil moisture content. Since $P=IV=I^2R$ where P is the applied power, I is the current, V is the voltage and R the resistance, for a constant total power applied to soil, the current and voltage applied will depend on the soil resistance R and, therefore, on the soil type and soil moisture.

For the tests shown in Table 2, a total power of 2500 W was applied to the soil. Two exposure times were used, a short exposure of 6 s and a long exposure of 12 s. The soil types were medium soil and sandy soil.

The resistance of the medium soil was greater than that of the sandy soil, as the currents were lower for the medium soil than the sandy soil for both a short exposure and a long exposure. The currents were larger for long exposure than for the short exposure for both soil types, showing that the soil was more moist for the long exposure than for the short exposure.

The untreated controls showed no disinfection. The treated soils all showed excellent disinfection for both soil types and both exposure times, being above 90% for all treated soils. As expected, disinfection was better for the longer exposure.

TABLE 2

Effectiveness of different currents and exposure times on disinfection of different types of soil

| # | Soil type | Exposure Time (s) | Current (A) | Power (W) | Disinfection Effectiveness (%) | Effect |
|---|---|---|---|---|---|---|
| 1 | Medium soil | 6 | 7.32 | 2500 | 94 | Excellent disinfection. |
| 2 | Medium soil | 6 | 7.23 | 2500 | 92 | Excellent disinfection. |
| 3 | Sandy soil | 6 | 8.12 | 2500 | 94 | Excellent disinfection. |
| 4 | Sandy soil | 6 | 8.45 | 2500 | 93 | Excellent disinfection. |
| 5 | Medium soil | 12 | 7.82 | 2500 | 95 | Excellent disinfection. |
| 6 | Medium soil | 12 | 8.28 | 2500 | 96 | Excellent disinfection. |
| 7 | Sandy soil | 12 | 8.69 | 2500 | 96 | Excellent disinfection. |
| 8 | Sandy soil | 12 | 9.83 | 2500 | 95 | Excellent disinfection. |
| 9 | Control- No treatment | — | — | — | 0 | No disinfection. |
| 10 | Control- No treatment | — | — | — | 0 | No disinfection. |

The terminology used herein is for the purpose of describing particular embodiments only and is not intended to be limiting of the invention. The corresponding structures, materials, acts, and equivalents of all means or step plus function elements in the claims below are intended to include any structure, material, or act for performing the function in combination with other claimed elements as specifically claimed.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The invention claimed is:

1. A motorized tracked vehicle for driving on land comprising
    an endless belt in mechanical contact with at least one propulsion roller, said endless belt being insulating;
    at least one sensor for detecting a soil condition comprising a member selected from a group consisting of soil humidity, soil conductivity, soil temperature or any combination thereof, said at least one sensor mounted on said vehicle;

at least one row of positive electrodes mounted on said endless belt for administering positive current and positive voltage to soil, each of said at least one row of positive electrodes comprising at least one positive electrode;

at least one row of negative electrodes mounted on said endless belt for administering negative current and negative voltage to soil, each of said at least one row of negative electrodes comprising at least one negative electrode;

an electrical power source for providing said positive current and said positive voltage to a portion of said at least one row of positive electrodes and said negative current and said negative voltage to a portion of said at least one row of negative electrodes;

at least one row of first power rollers, said at least one row of first power rollers being in electrical communication with at least one positive terminal of said electrical power source;

at least one row of second power rollers, said at least one row of second power rollers being in electrical communication with at least one negative terminal of said electrical power source;

at least one row of positive contact plates in electrical communication with each of said at least one row of first power rollers; each of said at least one row of positive contact plates configured to be in electrical communication with at least a portion of at least one of said at least one row of positive electrodes; and at least one row of negative contact plates in electrical communication with each of said at least one row of second power rollers; each of said at least one row of negative contact plates configured to be in electrical communication with at least a portion of at least one of said at least one row of negative electrodes;

a processor for processing said soil condition detected by said at least one sensor;

wherein said at least one row of first power rollers and said at least one row of positive contact plates are configured to administer said positive current and said positive voltage to a portion of said at least one row of positive electrodes, said portion of said at least one row of positive electrodes being configured to be embedded in said soil during said administration of said positive current and said positive voltage; and said at least one row of second power rollers and said at least one row of negative contact plates are configured to administer said negative current and said negative voltage to a portion of said at least one row of negative electrodes, said portion of said at least one row of negative electrodes being configured to be embedded in said soil during said administration of said negative current and said negative voltage; and said at least one processor is configured to determine from said soil condition transmitted by said at least one sensor, a value for each set of applied power selected from a group consisting of voltage, current, power level and any combination thereof required to kill or disable at least one type of pathogen;

and to instruct said electrical power source to apply said set of applied power to said at least one positive electrode and said at least one negative electrode.

2. The motorized tracked vehicle of claim 1, wherein a width of said endless belt is 160 cm.

3. The motorized tracked vehicle of claim 1, wherein a width of said endless belt is in a range from 50 cm to 800 cm.

4. The motorized tracked vehicle of claim 1, wherein the endless belt has a length in a range between 3 m and 15 m.

5. The motorized tracked vehicle of claim 1, wherein the endless belt has a length of 6 m.

6. The motorized tracked vehicle of claim 1, additionally comprising at least one power sensor selected from a group consisting of a voltage sensor, a current sensor, a power level sensor, and any combination thereof.

7. The motorized tracked vehicle of claim 1, wherein an absolute value of a voltage applicable all of said at least one positive electrode and all of said at least one negative electrode and any combination thereof is in a range from 1000 V to 9000 V.

8. The motorized tracked vehicle of claim 1, wherein an absolute value of a voltage applicable to all of said at least one positive electrode and all of said at least one negative electrode is 3000 V.

9. The motorized tracked vehicle of claim 1, wherein a power level applicable to all of said at least one positive electrode and all of said at least one negative electrode is in a range from 20000 W to 60,000 W.

10. A trailed implement for electrically disinfecting a soil in a land; said trailed implement comprising:
a power supply configured for generating high voltage;
an electrode arrangement comprising a base frame and at least two frame electrodes mounted therewithin and insertable into said soil;
each of said frame electrodes comprising a top bar, a bottom bar and a plurality of plate-like plow members mounted between said top bar and said bottom bar and perpendicular thereto;
said frame electrodes being electrically connected to said high voltage power supply such that said high voltage is applied between said at least two frame electrodes;
wherein at least one of said frame electrodes is reciprocally movable relative to said base frame in a direction of trailing of said implement.

11. The trailed implement according to claim 10, wherein each of said at least two frame electrodes is frame-shaped, with said top bar and said bottom bar oriented along said direction of trailing.

12. The trailed implement according to claim 10, wherein said plate-like plow members are mounted at an angle relative to said direction of trailing ranging between 5 and 90°.

13. The trailed implement according to claim 10, wherein said power supply is configured for generating at least one of AC high voltage and DC high voltage.

14. The trailed implement according to claim 10, wherein length L of said frame-shaped electrode along said direction of trailing ranges between 30 and 90 cm.

15. The trailed implement according to claim 10, wherein height H of said frame-shaped electrode ranges between 15 and 60 cm.

16. The trailed implement according to claim 10, wherein distance D between plate-like plow members within said frame-shaped electrode ranges between 4 and 10 cm.

17. The trailed implement according to claim 10, additionally comprising at least one sensor, the at least one sensor selected from a group consisting of a humidity sensor, a conductivity sensor, a temperature sensor, a voltage sensor, a current sensor, a power level sensor, and any combination thereof.

18. The trailed implement according to claim 10, wherein a voltage applicable to all of said at least two frame electrodes is in a range from 1000 V to 9000 V.

19. The trailed implement according to claim 10, wherein a voltage applicable to all of said at least two frame electrodes is 3000 V.

20. The trailed implement according to claim 10, wherein a power level applicable to all of said at least two frame electrodes is in a range from 20000 W to 60,000 W.

\* \* \* \* \*